United States Patent [19]
Romeas et al.

[11] Patent Number: 5,245,539
[45] Date of Patent: Sep. 14, 1993

[54] STEREOGRAPHIC X-RAY EXAMINATION SYSTEM INCLUDING GRAPHIC SCREEN MEANS FOR GENERATING INDEX MARKS TO LOCATE CORRESPONDING REGIONS IN DIFFERENT X-RAYS

[75] Inventors: René Romeas, Palaiseau; Bernard Pelissonnier, Montigny le Bretonneux; Yves Gregoire, Paris, all of France

[73] Assignee: General Electric CGR S.A., Issy les Moulineaux, France

[21] Appl. No.: 497,911

[22] Filed: Mar. 23, 1990

[30] Foreign Application Priority Data

Mar. 29, 1989 [FR] France .................. 8904087

[51] Int. Cl.⁵ .................. G06F 15/42
[52] U.S. Cl. .................. 364/413.13; 382/6
[58] Field of Search .......... 364/413.13; 386/6; 352/39, 41, 49, 57, 244; 356/396

[56] References Cited

U.S. PATENT DOCUMENTS

| | | | |
|---|---|---|---|
| 2,204,347 | 6/1940 | Files | 378/15.5 |
| 3,173,007 | 3/1965 | Maxwell | 378/15.5 |
| 4,063,100 | 12/1977 | Williams | 378/15.5 |
| 4,380,086 | 4/1983 | Vagi | 378/15.5 |
| 4,482,222 | 11/1984 | Stutz | 352/39 |
| 5,078,142 | 1/1992 | Siczek et al. | 128/653.1 |

FOREIGN PATENT DOCUMENTS 0272886  6/1988  European Pat. Off.
2115544  9/1983  United Kingdom.

OTHER PUBLICATIONS

Patent Abstracts of Japan, vol. 12, No. 334 (P-756) (3181), Sep. 8, 1988; & JP-A-63 96645, Apr. 27, 1988, T. Terada, "Ohp Device Using Liquid Crystal Panel".

*Primary Examiner*—Gail O. Hayes
*Attorney, Agent, or Firm*—Nilles & Nilles

[57] ABSTRACT

A light box for X-rays is made by using a graphics screen (20) coupled to a microprocessor (23), with the screen being used with inverse brightness. Under these conditions, the graphics screen emits light at nearly all points, other than special locations ($I^{25}$) whose positions can be controlled by means of a control box (24). An X-ray negative (6) to be examined is placed over the graphics screen. The control box is used to move the non-illuminated regions of the screen to point to special locations in the negative. The light box is particularly applicable t studying stereographic negatives for mammography. It makes it possible to determine more quickly and more accurately the locations of lesions in breasts under examination.

10 Claims, 2 Drawing Sheets

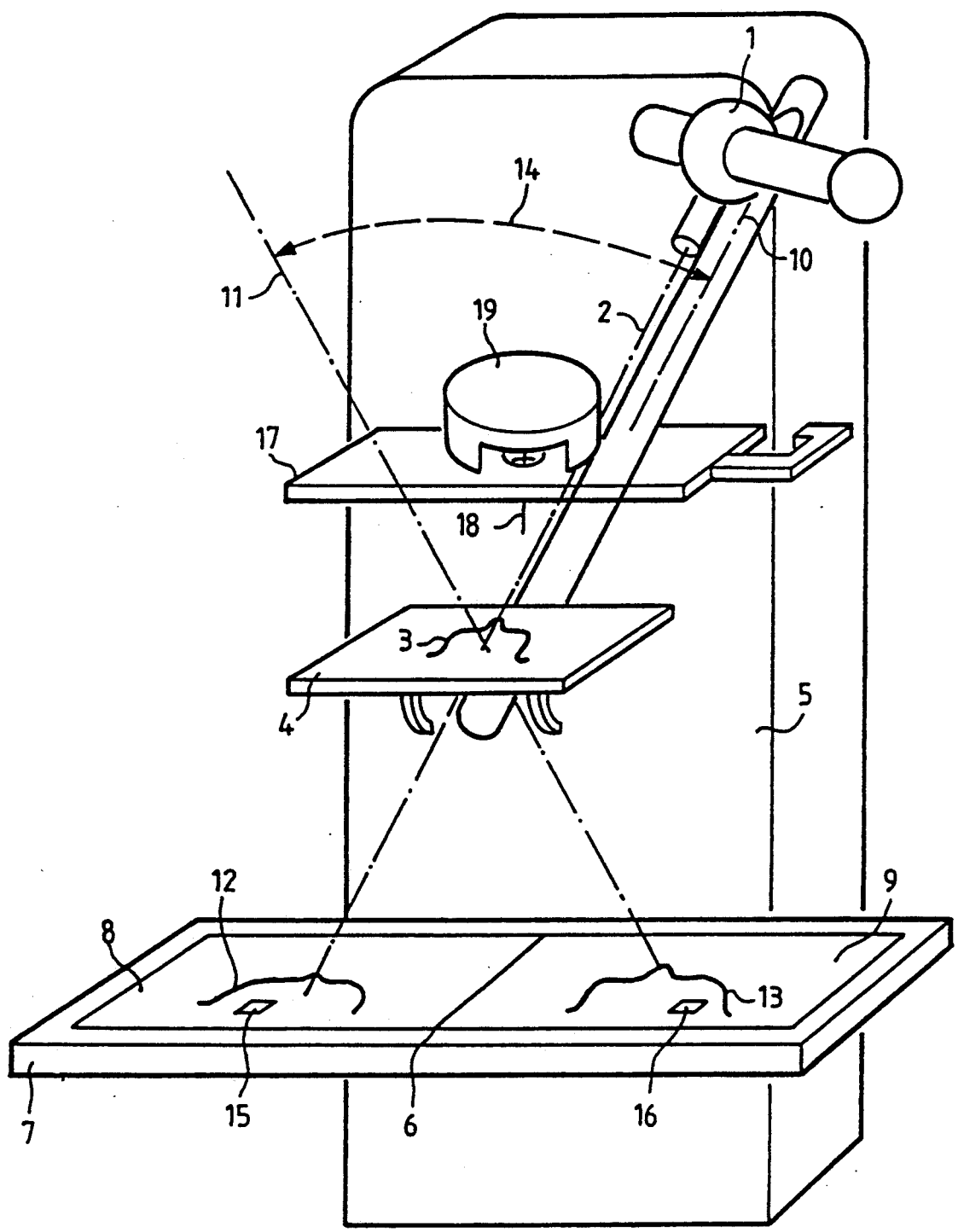
FIG_1
PRIOR ART

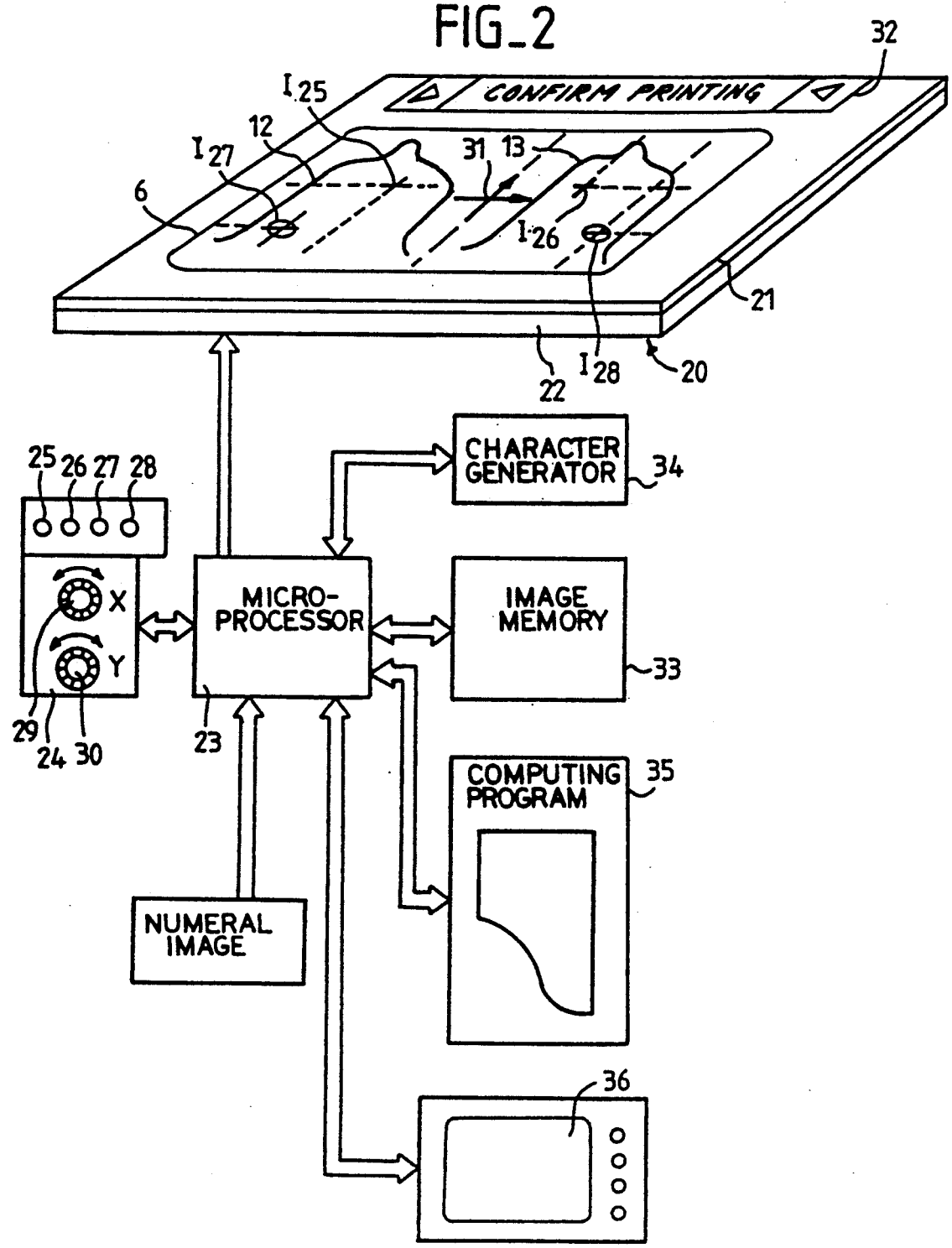

STEREOGRAPHIC X-RAY EXAMINATION SYSTEM INCLUDING GRAPHIC SCREEN MEANS FOR GENERATING INDEX MARKS TO LOCATE CORRESPONDING REGIONS IN DIFFERENT X-RAYS

The present invention relates to a light table, or light box, for X-rays. It is particularly applicable to medical applications where it is used for examining X-ray negatives. However, it may also be used in other applications. In a particularly advantageous implementation, the table of the invention is used for examining stereographic negatives: i.e. negatives corresponding to the body under examination being irradiated at two different angles. These negatives are presented simultaneously on the light box in order to make it easier for an observer or for a recognition machine to visualize in depth particular points in the body under examination or to locate them in three dimensions.

BACKGROUND OF THE INVENTION

Light boxes for X-rays are known in the prior art. They are essentially constituted by a translucent slab placed over lighting means. X-ray negatives to be examined are placed on the slab. The outlines and the structures which they represent are observed by differences in the attenuation of the light energy transmitted from the lighting means to the eye of the observer through the negative.

In stereotaxis examination for the purpose of determining the XYZ co-ordinates in three dimensions of a particular region of the body under examination (generally a lesion), two such negatives taken under two different angles of incidence are placed on the slab. Light boxes intended for this purpose also include moving spot index marks which make it possible to accurately locate points to be analyzed on the negatives. These index marks are generally driven by a mechanical device actuated by an operator. The operator actuates the mechanical device to bring the index marks into coincidence with the points to be analyzed on the film. A transcribing device records the mechanical displacements performed and transmits the corresponding position co-ordinates of the index mark to a computer. In conventional manner, the computer performs suitable processing to compute the three dimensional coordinates of a lesion on the basis of the positions of two index marks placed in like manner on each of the corresponding parts of the stereographic negative. The co-ordinates may be displayed on a video monitor or on any other appropriate means. They may also be used in a therapeutic treatment device or in a device for taking tissue samples for the purposes of cytological analysis.

In order to transmit the position of an index mark, the transcribing devices include a mechanical portion. The presence of this mechanical portion means that the transcribing devices have low accuracy. The exact position of the index mark is always transcribed with a degree of error because of bending or because of play. In addition, such transcribing devices are both expensive and heavy. Finally, because of their mechanical nature, they are liable to come out of adjustment and consequently they require frequent maintenance: cleaning, greasing, and recalibration. Such an apparatus is described in FR-A-2 248 535.

In addition, when examining stereographic negatives, it may be advantageous to have more than one pair of corresponding index marks available. Given the mechanical nature of the means for putting the index marks into place, it may be necessary to move a previously placed mark out of the way when placing a new mark because the mark-placing mechanisms, cannot overlap or crossover. That is why the maximum number of corresponding index mark pairs which can be used is small: the maximum known number being three.

The object of the invention is to remedy these drawbacks by providing a light box in which the slab and the lighting means beneath it are replaced by a graphics screen of one of the types now widely available commercially. In one example, the screen used is a matrix of light-emitting diodes (LEDs). It is also possible to use screens implementing other technologies: plasma screens; liquid crystal screens; or even cathode ray tubes.

Nevertheless, the graphics screen is used in a way which is different from the way in which such screens are normally used. A graphics screen normally comprises a plane which is not very bright: brightness occurs only at those locations which are to represent drawing lines. The invention proceeds differently. The screen is caused to emit light all over. It becomes dark only at points corresponding to the positions at which index marks are to be located. The screen must therefore have sufficient brightness to be about as bright as a current light box. In addition, the outside surface of the screen which is being used as a slab should preferably be flat. This means it can receive X-ray negatives without warping them.

A graphics screen is essentially characterized by its suitability for enabling the positions of its inverse brightness pixels (i.e. dark points) to be determined in an associated frame of reference. This may be achieved by any appropriate means. For example, position may be determined as a function of time within a frame of a video signal being displayed on the screen, with the time position of the pulse in this signal which corresponds to the dark portion being measured. If an image memory is used, then the addresses (the co-ordinates) of the dark points on the screen are directly related to the addresses of those memory cells in the image memory which contain information about the dark points (e.g. which contain a zero bit) unlike the remainder of the image which is bright (e.g. corresponding to one bits).

SUMMARY OF THE INVENTION

The present invention therefore provides a light box for X-rays, the table comprising a light-emitting surface for illuminating an X-ray negative placed on said surface, and at least one moving index mark which can be displaced over said surface to point to a particular location of the negative, wherein the table comprises a graphics screen controlled by a microprocessor to emit image-observation light at all points of the screen other than at points pointed to by an index mark.

In stereographic applications, there are a plurality of index marks. The positions of the index marks are correlated in pairs, and a conventional computer program reads the addresses of these index marks directly in order to determine which region of three dimensional space contains the object pointed to by the index marks.

BRIEF DESCRIPTION OF THE DRAWINGS

An embodiment of the invention is described by way of example with reference to the accompanying drawings, in which:

FIG. 1 is a diagram of a breast X-ray machine for obtaining a stereographic negative suitable for examination by making use of the invention; and FIG. 2 is a diagram of the essential means constituting a light box of the invention.

DETAILED DESCRIPTION

FIG. 1 shows an X-ray machine suitable for obtaining stereographic X-ray negatives of the breast. Like any other X-ray machine, this machine includes an X-ray tube 1 emitting X-rays along a main axis 2 towards a breast 3 to be X-rayed, which breast is supported on a support tray 4. The tray 4 is fixed to a frame 5 of the machine. After passing through the breast 3, the X-rays produce an image on a photosensitive plate 6 placed in a cassette 7. The cassette is held in place relative to the X-ray tube 1. A stereographic breast X-ray machine is also capable of making an image at different locations, on the same plate 6, e.g. on the left 8 or on the right 9 depending on whether the X-ray tube 1 is in a first orientation 10 or a second orientation 11 relative to the breast 3. These different orientations are made possible by carrying the tube 1 on a boom which rotates about a center of rotation. The images of the breast 3 are then projected respectively at locations 12 and 13 on the plate 6.

On the basis of the two images 12 and 13 which are thus preferably to be found side by side on a single negative, and which correspond to a known difference of angle of incidence 14, it is possible to point to matching characteristic regions, respectively 15 and 16, in each of these images and to use a computer to determine the position in three dimensions (e.g. above the breast-supporting tray 4) of a portion of the breast 3 whose shadows correspond to said matching regions. Under these conditions, it is possible to use a needle-carrying tray 17 including a biopsy needle 18 driven by a motor 19 to insert the needle into the breast 3 at the particular location from which tissue is to be taken for the purpose of analysis.

FIG. 2 shows a light box implementing the invention. The special feature of the light box of the invention is that it includes a graphics screen 20 which, in the preferred embodiment, comprises a transparent slab 21 placed over a plane grid 22 of light-emitting diodes (LEDs). The graphics screen 20 is controlled by a microprocessor 23 so that all of the LEDs in the grid 22 emit light. When the screen 20 is a plasma screen or a cathode ray screen, then the microprocessor generates a video signal such that all of the points on the screen are illuminated prior to any index marks being put into place.

A control box 24 is coupled to the microprocessor and has a set of knobs such as 25 to 28 for enabling one of the available index marks, e.g. $I_{25}$, to be selected. Once selected, the index marks $I_{25}$ to $I_{28}$ can be moved over the surface of the screen 20 by means of a set of potentiometers 29 and 30 for controlling X and Y displacements. The control box 24 is shown here merely by way of example. In particular, it may comprise control means which are more ergonomic, for example a mouse or a trackball. When the control box 24 is manipulated, instructions are sent to the microprocessor which cause it to display an index mark. As it does this, the microprocessor naturally stores in its memory the addresses of the positions of the index marks in terms of X and Y offsets relative to a reference mark 31 on the screen. Thereafter, given the pitch of the image points (pixels) on the graphics screen, it is easy to compute the co-ordinates of the positions of these index marks.

The accuracy of the device of the invention depends only on the linearity of the pixel pitch. The resolution with which the index marks can be put into place depends only on the pixel pitch of the graphics screen itself. For a given graphics screen, these two parameters are fixed by construction. Given the production technology for graphics screen masks, these positions are thus very accurate and easily reproducible from one screen to another. In one example, using 10 cm ×20 cm screens, suitable for stereotaxy in mammography, it is easy to find screens having a pixel pitch of about 0.25 mm to 0.3 mm. This is sufficiently accurate. It can immediately be seen that a device made in this way cannot go out of adjustment. Its accuracy is obtained by construction and not by (frequently repeated) adjustments of a mechanical linkage. In addition, there is no wear, and thus very little maintenance, thereby ensuring that the apparatus is very reliable. Finally, the falling prices of electronic components make it possible to anticipate production costs which are considerably lower than present costs.

However using a graphics screen together with a microprocessor also provides much greater operator comfort. In particular, a character generator 34 can be used for distinguishing various types of associated pairs of corresponding index marks. For example, index marks $I_{25}$ and $I_{26}$ may be represented by small crosses, whereas index marks $I_{27}$ and $I_{28}$ may be represented by small crosses within respective circles. It can immediately be seen that by selecting a different type of character in this way, the index marks can be associated in as many pairs as desired, and also that by using a microprocessor associated with a graphics screen, it is possible to displace the index marks without worrying about possible mechanical linkage overlaps. The characters displayed as index marks may also be distinguished from each other by brightness: e.g. by being brighter than the background. They may also be distinguished by color, if the graphics screen is a color screen. An index mark may therefore correspond to a single pixel or to a plurality of pixels on the screen. Similarly, by reserving a region 32 at the periphery of the screen 20, the character generator can be used to write messages such as "CONFIRM POINTING", thereby informing the operator who is manipulating the control box 24 how to perform the next expected operation.

In addition, the light box of the invention makes all sorts of improvements possible. For example, the positioning of the film 6 on the surface of the slab 21 can be replaced by injecting a digital representation of the image of the film 6. Transforming an X-ray image into a digital image is common practice. The digital image can then be stored via the microprocessor 23 in an image memory 33. The image memory 33 is read by the microprocessor 23 and is displayed on the graphics screen 20 simultaneously with its display of the index marks $I_{25}$ to $I_{28}$.

As mentioned above, it is known how to perform the processing required for computing the co-ordinates of a lesion. The microprocessor 23 may be capable of running a program 35 for performing this processing. When processing is completed, it can deliver data representative of the position in three dimensions of the point specified by combined examination of the two stereographic images together. This information may be displayed on a display monitor 36. This information may also be used for controlling the motor 19 for displacing the biopsy needle 18.

In order to make this chain more effective, the film 6 contained in the cassette 7 may be replaced by an X-ray image intensifier screen. The video signal delivered by this intensifier screen can be processed and transformed into a digital image which can be displayed directly on the graphics screen 20. The operator who performs the stereographic examination can then manipulate the control box 24 to inform the microprocessor 3 of the corresponding positions of the points to be treated. The microprocessor 23 then runs the program 35 and can control the motor 19, almost in real time. This can accelerate therapy which a patient always finds arduous.

What is claimed is:

1. Utilization process of a light table for x-rays, said table comprising a graphics screen, said process comprising the following steps:

placing a stereographic x-ray negative of a body on said table, and illuminating said x-ray negative;

displacing at least two moving index marks over said table under the control of a microprocessor to point to particular locations of the negative;

controlling said graphics screen by said microprocessor to emit image-observation light at all points of the screen other than at points pointed to by said index marks; and determining, by said microprocessor, a position, in a three dimensions space, of a particular location into said body using addresses of said points.

2. A light table for x-rays, said table comprising: a microprocessor; and a graphics screen, controlled by said microprocessor, for illuminating a sterographic x-ray negative of a body placed on said table, and for moving at least two index marks which can be displaced over a surface of said table to point to particular locations of the negative, said screen including means for emitting an image-observation light at all points of the screen other than at points pointed to by said index marks, and wherein the microprocessor includes means for associating the addresses of these points for determining a position in a three dimensional space of a particular location into said body.

3. A light table according to claim 2, wherein the microprocessor reserves a region of the surface of the graphics screen, for writing messages in the form of text.

4. A light table according to claims 2 or 3, also including an image memory controlled by the microprocessor to directly display on the graphics screen a digitized version of the X-ray negative to be examined.

5. A light table according to claims 2 or 3, wherein the graphics screen is of the plasma type.

6. A light table according to claims 2 or 3, wherein the graphics screen is of the liquid crystal type.

7. A light table according to claims 2 or 3, wherein the graphics screen is of the cathode ray tube type.

8. A light table according to claims 2 or 3, wherein the graphics screen is of the light-emitting diode matrix type.

9. A light table according to claims 2 or 3, wherein the microprocessor includes a character generator for displaying on the graphics screen a plurality of index marks differing in at least one of shape and brightness.

10. A light table according to claim 3, wherein said region is a peripheral region.

* * * * *